United States Patent
Xiao et al.

(10) Patent No.: US 12,097,110 B2
(45) Date of Patent: Sep. 24, 2024

(54) COVERED STENT

(71) Applicant: Lifetech Scientific (Shenzhen) Co., Ltd., Shenzhen (CN)

(72) Inventors: Benhao Xiao, Shenzhen (CN); Caiping Liu, Shenzhen (CN); Da Li, Shenzhen (CN)

(73) Assignee: Lifetech Scientific (Shenzhen) Co., Ltd., Shenzhen (CN)

(*) Notice: Subject to any disclaimer, the term of this patent is extended or adjusted under 35 U.S.C. 154(b) by 0 days.

(21) Appl. No.: 17/954,175

(22) Filed: Sep. 27, 2022

(65) Prior Publication Data

US 2023/0016711 A1 Jan. 19, 2023

Related U.S. Application Data

(63) Continuation of application No. 16/957,871, filed as application No. PCT/CN2018/120323 on Dec. 11, 2018, now Pat. No. 11,471,265.

(30) Foreign Application Priority Data

Dec. 27, 2017 (CN) .......................... 201711446195.2
Dec. 27, 2017 (CN) .......................... 201711446263.5

(51) Int. Cl.
*A61F 2/07* (2013.01)
*A61F 2/86* (2013.01)

(52) U.S. Cl.
CPC .......... *A61F 2/07* (2013.01); *A61F 2002/077* (2013.01)

(58) Field of Classification Search
None
See application file for complete search history.

(56) References Cited

U.S. PATENT DOCUMENTS

| | | | | |
|---|---|---|---|---|
| 5,824,037 A * | 10/1998 | Fogarty | ..................... | A61F 2/07 623/1.13 |
| 5,911,754 A * | 6/1999 | Kanesaka | .................. | A61F 2/91 606/198 |
| 6,998,060 B2 * | 2/2006 | Tomonto | .................. | A61F 2/915 216/49 |
| 7,128,756 B2 * | 10/2006 | Lowe | ...................... | A61F 2/915 623/1.15 |
| 7,811,314 B2 * | 10/2010 | Fierens | .................... | A61F 2/915 623/1.15 |
| 7,887,578 B2 * | 2/2011 | Schneider | ............... | A61F 2/915 606/198 |

(Continued)

FOREIGN PATENT DOCUMENTS

| WO | WO-2007050070 A1 * | 5/2007 | ................ | A61F 2/91 |
|---|---|---|---|---|
| WO | WO-2017047569 A1 * | 3/2017 | ................ | A61F 2/07 |

*Primary Examiner* — Ann Schillinger
(74) *Attorney, Agent, or Firm* — Raymond Sun

(57) ABSTRACT

A stent graft comprises a plurality of wavy rings sequentially arranged in a spaced manner, and membranes fixed to the plurality of wavy rings, wherein the stent graft comprises, in a circumferential direction, at least one keel region and a non-keel region connected to the keel region, the keel region having an axial shortening rate that is less than that of the non-keel region, and the axial shortening rate of the keel region is 10-40%. The stent graft can be bent in all directions, and the keel region on the stent graft can provide a sufficient amount of an axial support force for the stent.

10 Claims, 7 Drawing Sheets

(56) References Cited

U.S. PATENT DOCUMENTS

| | | | | |
|---|---|---|---|---|
| 8,016,874 B2* | 9/2011 | Casey | ............... | A61F 2/91 |
| | | | | 623/1.15 |
| 8,128,626 B2* | 3/2012 | Justin | ............... | A61B 17/7233 |
| | | | | 606/86 R |
| 8,337,544 B2* | 12/2012 | Osman | ............... | A61F 2/91 |
| | | | | 623/1.2 |
| 10,238,513 B2* | 3/2019 | Ta | ............... | A61F 2/89 |
| 11,471,265 B2* | 10/2022 | Xiao | ............... | A61F 2/07 |
| 2002/0052644 A1* | 5/2002 | Shaolian | ............... | A61F 2/856 |
| | | | | 623/1.13 |
| 2003/0088305 A1* | 5/2003 | Van Schie | ............... | A61F 2/06 |
| | | | | 623/1.12 |
| 2004/0215325 A1* | 10/2004 | Penn | ............... | A61F 2/91 |
| | | | | 623/1.15 |
| 2006/0155366 A1* | 7/2006 | LaDuca | ............... | A61F 2/954 |
| | | | | 606/108 |
| 2007/0208421 A1* | 9/2007 | Quigley | ............... | A61F 2/07 |
| | | | | 623/1.44 |
| 2008/0119943 A1* | 5/2008 | Armstrong | ............... | A61F 2/89 |
| | | | | 623/23.7 |
| 2009/0125095 A1* | 5/2009 | Bui | ............... | A61F 2/07 |
| | | | | 623/1.13 |
| 2009/0163994 A1* | 6/2009 | Quigley | ............... | A61F 2/07 |
| | | | | 623/1.15 |
| 2010/0198333 A1* | 8/2010 | Macatangay | ............... | A61F 2/88 |
| | | | | 623/1.15 |
| 2011/0004292 A1* | 1/2011 | Davis | ............... | A61F 2/915 |
| | | | | 623/1.16 |
| 2011/0106237 A1* | 5/2011 | Bonsignore | ............... | A61F 2/915 |
| | | | | 623/1.15 |
| 2013/0079870 A1* | 3/2013 | Roeder | ............... | A61F 2/07 |
| | | | | 623/1.35 |
| 2018/0008394 A1* | 1/2018 | Marmur | ............... | A61F 2/07 |

* cited by examiner

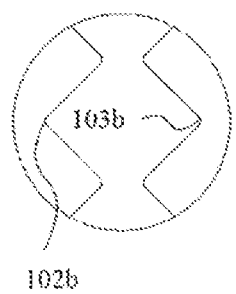 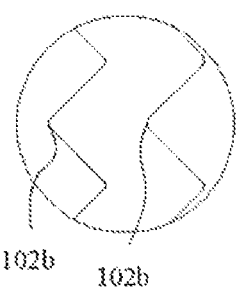 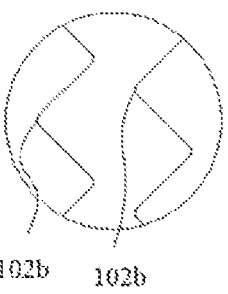
Fig.10a　　　　Fig.10b　　　　Fig.10c
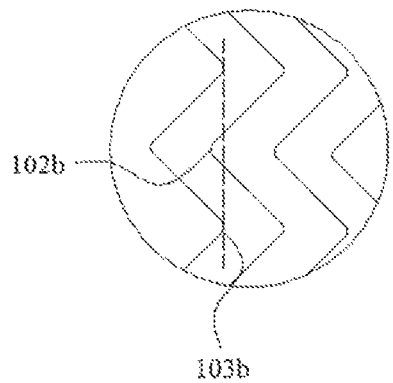
Fig.11
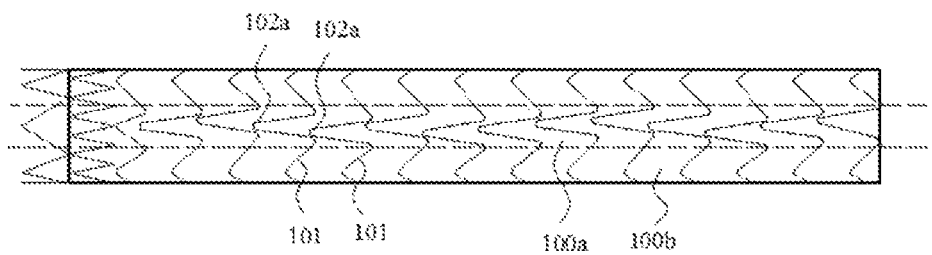
Fig.12
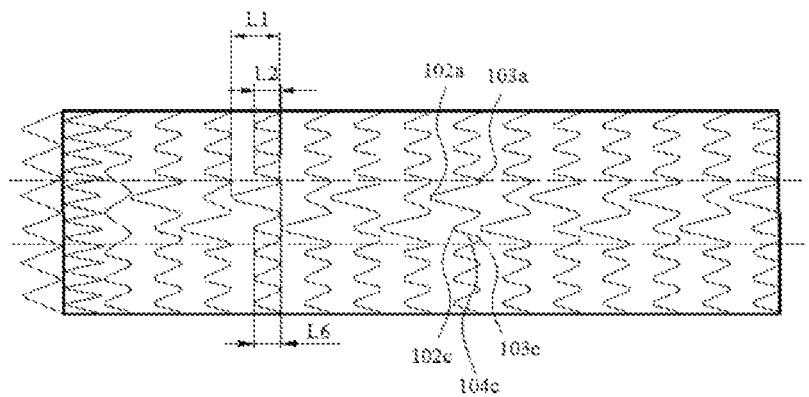
Fig.13

COVERED STENT

FIELD

The disclosure relates to the technical field of medical apparatuses, and in particular, to a stent graft.

BACKGROUND

An aneurysm is a common vascular disease, mostly occurring in the elderly, which easily leads to the rupture of aortic aneurysms and poses a great threat to the life of patients. General surgery was considered as the only way to treat aortic aneurysms, but this method is extremely dangerous.

With the continuous development of medical technology, surgeries such as a minimally invasive surgery which implants a stent graft into a human body for treatment of aortic aneurysm and dissecting aneurysm are being used more and more. In this treatment method, an artificial stent graft is compressed into a delivery device, and guided into a human body along a previously implanted guide wire, where the stent graft is released to a lesion position. A tumor cavity is isolated to form a new blood flow channel, and after an aneurysm loses blood flow supply, residual blood in the tumor cavity gradually forms blood clots and is muscularized into vascular tissues, and a tumor wall in an expanded state contracts due to negative pressure and gradually returns to an original state, thereby achieving the treatment of the aneurysm.

At present, the stent graft mainly includes a plurality of metal rings which are sequentially arranged in a spaced manner, and a membrane fixed to the plurality of metal rings to connect the plurality of metal rings. Due to the fact that the adjacent metal rings are merely in a flexible connection through the membrane, and due to the lack of rigid constraints, the metal rings are easily shortened during stent release and post-operation long-term use, so the stent can possibly enter a tumor cavity when the stent shortens from a distal end to a proximal end, leading to a failure to completely cover a tumor body by the stent graft, and causing a type I internal leakage. In order to avoid the above situation, the prior art mostly adopts an additional rigid connector between the adjacent metal rings to prevent the stent from shortening.

However, the rigid connector limits the bending direction of the stent so that the stent can only be curved towards a side facing away from the connector. As a result, the rigid connector is usually placed on a greater curvature side of the stent. However, blood vessels of the human body are complicated in structure and are usually in a curved state. Since the stent cannot be bent arbitrarily due to the rigid connector, the stent cannot be easily adapted to the shapes of the blood vessels.

SUMMARY

The technical problem to be solved by the present disclosure is to provide a stent graft capable of being bent in all directions to overcome the above-mentioned defects in the prior art.

In order to solve the technical problem, the technical solution of the disclosure is as follows:

Provided is a stent graft, including a plurality of wavy rings and a membrane connected and fixed to the plurality of wavy rings. The stent graft includes, in a circumferential direction, at least one keel region and a non-keel region connected with the keel region, wherein the shortening rate of the keel region is less than the shortening rate of the non-keel region, and the shortening rate of the keel region is 10-40%.

Provided is a stent graft, including a first body section and a second body section connected with the first body section, which are distributed in the axial direction, wherein the axial shortening rate of the first body section is 10-40%, and the axial shortening rate of the second body section is zero.

In summary, the stent graft of the disclosure has the following beneficial effects: the stent graft of the application which is of an axial compressible structure can be bent towards all directions, the stent graft is provided with at least one keel region and a non-keel region, the shortening rate of the stent graft compressed in the axial direction in the keel region is less than the shortening rate of the stent graft compressed in the axial direction in the non-keel region, and when the stent graft is bent, the wavy rings in the keel region are prone to abutting against each other to form a rigid axial supporting structure on the stent graft to prevent the stent graft from continuing to shorten, therefore, the stent graft of the application can not only meet various bending requirements on a stent, but can also provide enough axial supporting force for the stent.

BRIEF DESCRIPTION OF THE DRAWINGS

The disclosure will be further described in combination with accompanying drawings and embodiments. In drawings:

FIG. 10a is a schematic diagram of adjacent second wavy segments of the stent graft shown in FIG. 1 being opposite in phase when the adjacent second wavy segments have no overlap in the axial direction;

FIG. 10b is a schematic diagram of the adjacent second wavy segments of the stent graft shown in FIG. 1 being identical in phase when the adjacent second wavy segments have no overlap in the axial direction;

FIG. 10c is a schematic diagram of the adjacent second wavy segments of the stent graft shown in FIG. 1 having a phase difference when the adjacent second wavy segments have no overlap in the axial direction;

FIG. 11 is a schematic diagram of the adjacent second wavy segments of the stent graft shown in FIG. 1 which have overlaps in the axial direction;

FIG. 12 is a structural schematic diagram of a stent graft provided by a second preferred embodiment of the present disclosure;

FIG. 13 is a structural schematic diagram of a stent graft provided by a third preferred embodiment of the present disclosure;

DETAILED DESCRIPTION OF THE EMBODIMENTS

In order that the technical features, objects and effects of the present embodiments may be more clearly understood, specific embodiments thereof will now be described in detail with reference to the accompanying drawings.

It should be noted that "distal" and "proximal" are used as orientation words, which are customary terms in the field of interventional medical apparatuses, the "distal" means an end away from an operator during a surgical procedure, and the "proximal" means an end close to the operator during the surgical procedure. An axial direction refers to a direction which is parallel to the connecting line of a distal center and a proximal center of a medical apparatus; a radial direction refers to a direction perpendicular to the axial direction; and the distance from the axis refers to the distance reaching the axis in the radial direction.

Figure 1:
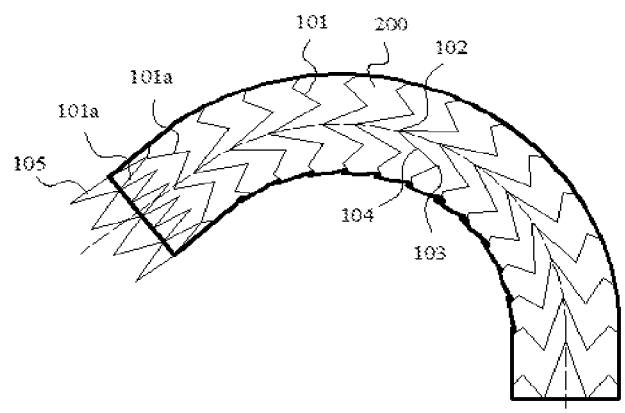
FIG. 1 is a structural schematic diagram of a straight tubular stent graft provided by a first preferred embodiment of the present disclosure in a bent state.

As shown in FIG. 1, a first preferred embodiment of the present disclosure provides a stent graft which is substantially of an open-ended and hollow tubular structure, the stent graft including a plurality of wavy rings 101, and membranes 200 fixed to the plurality of the wavy rings 101 to connect the plurality of the wavy rings 101.

The membranes 200 are tubular cavity structures where the middle is closed and the ends are opened, and made of high molecular materials having good biocompatibility, such as e-PTFE, PET, or the like. The membranes 200 are fixed to the plurality of wavy rings 101 and enclosed to form a tube cavity with a longitudinal axis, and the tube cavity serves as a channel through which blood flows when the stent graft is implanted into a blood vessel.

The wavy rings 101 are made of materials having good biocompatibility, such as nickel titanium, stainless steel, or the like. The plurality of wavy rings 101 are arranged sequentially in a spaced-apart manner from a proximal end to a distal end, and preferably arranged in a parallel spaced manner. Each wavy ring 101 is of a closed cylindrical structure, and includes a plurality of proximal vertices 102, a plurality of distal vertices 103, and supporting bodies 104 connecting the adjacent proximal vertices 102 and distal vertices 103, and the proximal vertices 102 and distal vertices 103 are wave crests and troughs of corresponding waves, respectively. The plurality of wavy rings 101 have the same or similar wavy shapes, for example, the wavy rings 101 may be a Z-shaped wave, an M-shaped wave, a V-shaped wave or sinusoidal wave structures, or of other structures that are radially compressible to a very small diameter. It will be appreciated that the embodiment does not limit the specific structures of the wavy rings 101, the wave shapes of the wavy rings 101 may be set as required, and the number of waves and the heights of the waves in each wavy ring 101 may be set as required.

The stent graft may be prepared as follows: weaving a metal wire into a required wave shape, the metal wire may be a nickel-titanium alloy wire with a wire diameter of, for example, 0.35 mm; and after heat setting, surrounding two end portions of the metal wire with a steel jacket and fixing by mechanical pressing so that the metal wire and the steel jacket are connected and fastened to form a metal ring. After all the wavy rings 101 are manufactured, surfaces of the wavy rings 101 which are sequentially arranged are covered with membranes. For example, inner surfaces and outer surfaces of the plurality of wavy rings 101 may be integrally covered with e-PTFE membranes so that the plurality of wavy rings 101 are located between two membranes 200, and the e-PTFE membranes of an inner layer and an outer layer are bonded together by high-temperature pressing, thereby fixing the plurality of wavy rings 101 between the two membranes. It will be appreciated that, in other embodiments, the wavy rings 101 may also be sutured to PET membranes.

Of course, when formed by integrally cutting a metal tube, the wavy rings 101 are not required to be fixedly connected by the steel jacket. Alternatively, the wavy ring may be formed by welding two end points of the metal wire.

Figure 2:
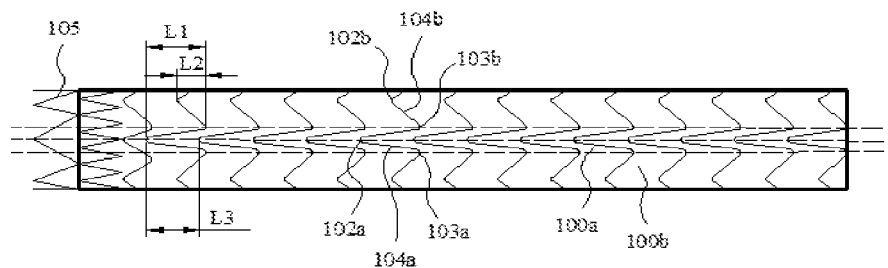
FIG. 2 is a structural schematic diagram of the stent graft shown in FIG. 1 in a natural state.

Referring to FIG. 2, the stent graft includes, in a circumferential direction, at least one keel region 100a and a non-keel region 100b connected with the keel region 100a, the keel region 100a and the non-keel region 100b both extending in the axial direction of the stent graft, and the region enclosed by the dotted lines in FIG. 2 is the keel region 100a.

The axial shortening rate of the keel region 100a of the stent graft is less than the axial shortening rate of the non-keel region 100b, and the axial shortening rate of the stent graft in the keel region 100a is 10-40%.

A method for calculating the shortening rate of the stent graft in the axial direction is as follows: taking the length of the stent graft, which is in a straight tubular shape, in the axial direction in a natural state as r and the diameter of the stent graft as d1, surrounding an inner tube with the diameter of d2 (d2 is less than d1, preferably d2 is equal to 90%*d1) with the stent graft, applying pressure F ($1N \leq F \leq 2N$) in the axial direction to the stent graft till the stent graft cannot shorten anymore to obtain the total length s, and calculating the axial shortening rate of the stent graft according to the formula (r−s)/r×100%. Where: (r−s) is an available maximum shortening value of the stent graft. The stent graft surrounds the inner tube for shortening, so that the phenomenon that the stent graft is folded when shortening can be effectively avoided, that is, (r−s) of the present application is the available maximum shortening value when the stent graft is not folded.

When the stent graft is in a frustum shape, that is, the diameters of the two ends of the stent graft are different, the length of the stent graft in the axial direction in the natural state is r, the diameter of the large end is d1, the diameter of the small end is d3, the stent graft surrounds a conical inner tube or a frustum inner tube with the same taper as the stent graft, and the perpendicular distance between the stent graft and the conical inner tube or the frustum inner tube is 0.05d1. The position of the small end of the stent graft is fixed and unchanged, the pressure F (1N≤F≤2N) in the axial direction is applied to the large end, and the total length of the stent graft when the stent graft cannot shorten anymore is s, and thus the shortening rate of the stent graft in the axial direction is (r−s)/r 100%. Where: (r−s) is an available maximum shortening value of the stent graft. The stent graft surrounds the inner tube for shortening, so that the phenomenon that the stent graft is folded when shortening can be effectively avoided, that is, (r−s) of the present application is the available maximum shortening value when the stent graft is not folded.

Figure 3:
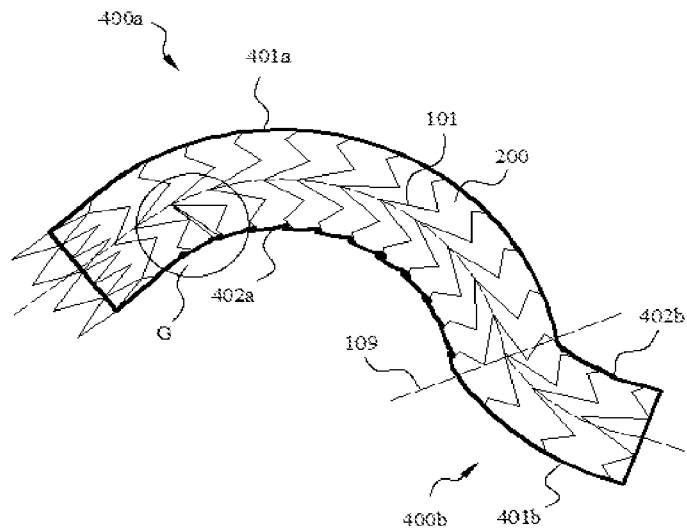
FIG. 3 is a structural schematic diagram of a bent stent graft provided by a first preferred embodiment of the present disclosure.
Figure 4:
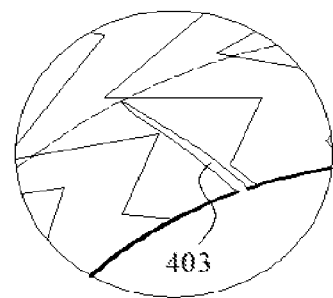
FIG. 4 is an enlarged view of a portion G of the stent graft shown in FIG. 3.
Figure 5:
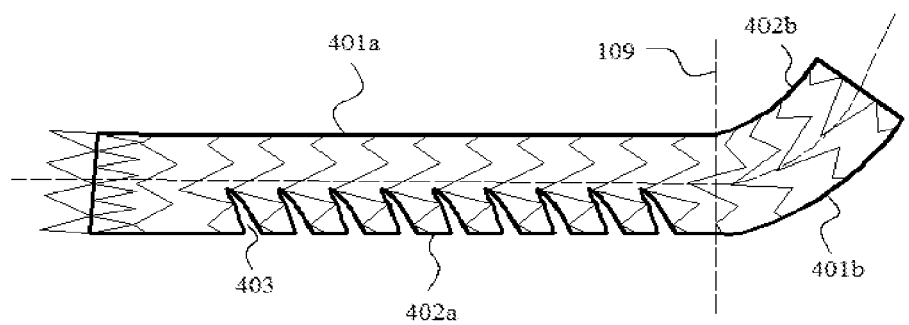
FIG. 5 is a structural schematic diagram of a first bent segment of the stent graft shown in FIG. 3 after being straightened along a first profile line.
Figure 6:
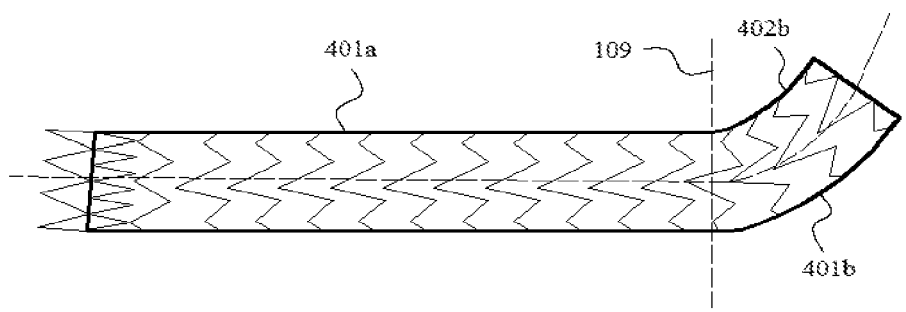
FIG. 6 is a structural schematic diagram of wavy rings of the stent graft shown in FIG. 3 after being re-arranged in an axial direction according to a wave spacing between the wavy rings at the first profile line and covered with membranes.

When the stent graft itself is manufactured into a bent shape, as shown in FIG. 3, the stent graft includes a first bent section 400a and a second bent section 400b, the first bent section 400a has a first profile line 401a on a greater curvature side of the first bent section 400a and a second profile line 402a on a lesser curvature side of the first bent section 400a, and the second bent section 400b has a third profile line 401b on a greater curvature side of the second bent section 400b and a fourth profile line 402b on a lesser curvature side of the second bent section 400b. At this time, there are two methods for calculating the shortening rate of the bent section of the stent graft. One method is as follows: referring together to FIG. 4, by taking the first bent section 400a as an example, partitioning the first bent section 400a with a plane 109 perpendicular to the axial direction of the stent graft; and cutting a plurality of notches 403 in the membranes 200 close to the second profile line 402a. The sizes of the notches 403 can ensure that the stent graft is straightened along the first profile line 401a (or cutting a plurality of notches 403 in the membranes 200 close to the second profile line 402a, so that the sizes of the notches 403 can exactly ensure that the stent graft is straightened along the first profile line 401a). After the first bent section 400a is straightened as shown in FIG. 5, obtaining the length r and the diameter d1 of the straightened first bent section 400a; then surrounding an inner tube with a diameter of d2 (d2 is less than d1, preferably d2 is equal to 90%*d1) with the straightened first bent section 400a; applying pressure F (1N≤F≤2N) in the axial direction to the stent graft until the stent graft cannot shorten, so as to obtain the total length s of the region B; and then calculating the axial shortening rate of the stent graft in the region B according to the formula (r−s)/r*100%. The other method is as follows: also by taking the first bent section 400a as an example, re-arranging the wavy rings 101 in the axial direction according to the wave spacing between the wavy rings 101 at the first profile line 401a, covering the wavy rings 101 with membranes (with the covering materials and a selected process kept consistent with those of the original stent), as shown in FIG. 6, and then calculating the shortening rate according to the above-mentioned method for calculating the shortening rate.

Figure 7:
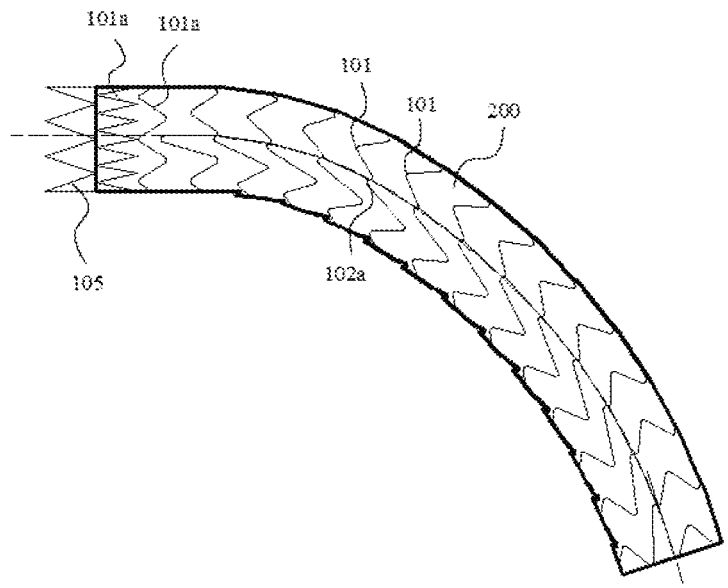
FIG. 7 is a structural schematic diagram of the wavy rings of the stent graft shown in FIG. 1 which abut against each other.

During the bending of the stent graft, when any one of the keel region 100a or the non-keel region 100b reaches the available maximum shortening value, a rigid axial supporting structure is formed in the region to prevent the stent graft from continuing to be bent. Referring to FIG. 7, during the bending of the stent graft, one wavy ring 101 of the stent graft moves in the direction of pressure together with portions of the membranes 200 fixed to the wavy ring 101; the portions of the membranes 200 fixed to the wavy ring 101 move together with portions of the membranes 200 distributed at the periphery of the wavy ring 101. The portions of the membranes 200 distributed at the periphery of the wavy ring 101 will immediately pull another wavy ring 101 nearby to move towards one side close to the wavy ring 101 until the wavy ring 101 cannot keep moving, and at this time, a rigid axial supporting structure is formed on the stent graft, so that the stent graft is prevented from continuing to shorten anymore.

When the axial shortening rate of the stent graft in the keel region 100a is less than 10%, the shortening rate of the keel region 100a is too small, and no matter to which direction the stent graft is bent, the keel region 100a easily reaches the available maximum shortening value, and the keel region 100a cannot shorten anymore, thereby restricting the stent graft from continuing to be bent. When the axial shortening rate of the stent graft in the keel region 100a is greater than 40%, the axial supporting effect of the stent graft is poor, and the stent graft may enter the tumor cavity when the distal end of the stent graft shortens towards the proximal end of the stent graft, thus threatening the life of a patient. When the shortening rate of the stent graft in the keel region 100a is 10-40%, the stent graft can be bent towards all directions to adapt to bent blood vessels, and sufficient axial support can be provided to prevent axial shortening for the stent graft, thus maintaining the tube cavity shape of the stent graft. Referring to FIG. 3, the stent graft may be continuously bent towards different directions to better adapt to a bent blood vessel. Preferably, the axial shortening rate of the stent graft in the keel region 100a is 20-30%.

Figure 8:
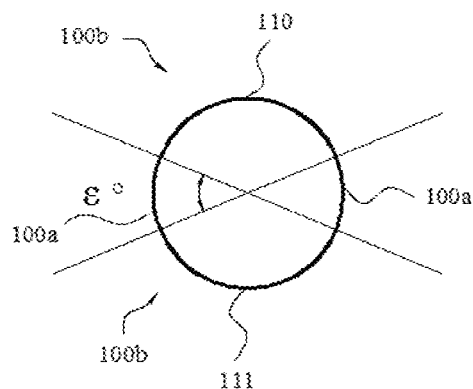
FIG. 8 is a structural schematic diagram of keel regions of the stent graft shown in FIG. 1 that are distributed on an outer surface of the stent graft.

Referring to FIG. 8, the circumferential angle covered by the keel region 100a on an outer surface of the stent graft is ε° which is greater than or equal to 15° and less than or equal to 45°. When ε° is less than 15°, the circumferential angle covered by the keel region 100a on the outer surface of the stent graft is small, which may lead to a poor axial supporting effect of the entire stent graft, and the stent graft may easily swing and retract under the impact of blood flow, finally causing the stent graft to retract into the tumor cavity, and endangering the life of the patient. When ε° is greater than 45°, the circumferential angle covered by the keel region 100a on the outer surface of the stent graft is large, which is not conducive to stent bending. When ε° is greater than or equal to 15° and less than or equal to 45°, sufficient axial support can be provided for the stent graft, and when the stent graft is applied to a blood vessel with greater curvature, no folding occurs, thereby keeping the tube cavity smooth, and enabling the stent graft to adapt to a wider range of vascular morphology.

Preferably, the circumferential angle E° covered by each keel region 100a on the outer surface of the stent graft is in the range of 20°-30°. In addition, the number of the keel regions 100a is two, and the two keel regions 100a are symmetrically distributed in the circumferential direction of the stent graft.

As shown in FIG. 2, the wavy rings 101 include first wavy segments located in the keel regions 100a and second wavy segments located in the non-keel region 100b, and the wave heights of the first wavy segments are greater than the wave heights of the second wavy segments. Where the wave height of the first wavy segment is L1, the wave height of the second wavy segment is L2, and L1 and L2 meet the condition that L2/L1 is greater than or equal to ⅓ and less than 1. When L2/L1 is less than ⅓, dense distribution of local waves in the keel regions 100a is easily caused, which affects the bending property of the stent graft at this position; or sparse distribution of local waves in the non-keel region 100b is caused, which results in a poor supporting effect of the stent graft at this position and a high probability of deformation. Preferably, L2 is greater than or equal to 4 mm and less than or equal to 12 mm, which not only is conducive to processing, but also improves the bending property of the stent graft. Specifically, each first wavy segment includes at least one first proximal vertex 102a, at least one first distal vertex 103a, and a first supporting body 104a connecting the adjacent first proximal vertex 102a and first distal vertex 103a, and the second wavy segment includes at least one second proximal vertex 102b, at least one second distal vertex 103b, and a second supporting body 104b connecting the adjacent second distal vertex 102b and second distal vertex 103b. The wave height of the first wavy segment refers to the distance between the first proximal vertex 102a and the first distal vertex 103a in the axial direction. The wave height of the second wavy segment refers to the distance in the axial direction between the second proximal vertex 102b and the second distal vertex 103b; and in the illustrated embodiment, the first distal vertex 103a and the second distal vertex 103b are located in the same plane perpendicular to the longitudinal central axis of the stent graft.

The distance in the axial direction between the first proximal vertex 102a of the first wavy segment of the wavy ring 101 and the corresponding first proximal vertex 102a of the adjacent wavy ring 101 is L3. L1 and L3 meet the condition that L3/L1 is greater than or equal to ¼ and less than or equal to 3/2, so that wave distribution in the keel regions 100a is relatively uniform. Preferably, L1 is greater than or equal to 8 mm and less than or equal to 18 mm, and most preferably, L1 is greater than or equal to 12 mm and less than or equal to 14 mm.

Since the wavy ring 101 has at least one wave crest with high wave height in the keel region 100a and the plurality of distal vertices 103 are located in the same plane perpendicular to the longitudinal axis, when the stent graft shortens, the first proximal vertex 102a of one wavy ring 101 easily abuts against another wavy ring 101, and the wavy rings 101 in the keel region 100a abut against each other. When the wavy rings 101 in the keel region 100a abut against each other, a rigid axial supporting structure is formed on the stent graft to prevent the stent from continuing to shorten. By arranging the keel regions 100a on the stent graft, various bending requirements of the stent graft can be met, and sufficient axial supporting force can be provided for the stent graft, thereby preventing the stent graft from shortening into the tumor cavity.

In this embodiment, each first wavy segment includes one first proximal vertex 102a therein, a connecting line between the first proximal vertices 102a of two adjacent first wavy segments is parallel to the axis of the stent graft, and the first supporting bodies 104a connected with two sides of the first proximal vertex 102a are symmetrically disposed with respect to the axis of the stent graft.

Further, the first wavy segment of the keel region 100a has a wave included angle of 30°-60°, and the second wavy segment of the non-keel region 100b has a wave included angle of 70°-120°. The wave included angle refers to an included angle between the supporting bodies 104 connected with the two sides of the same proximal vertex 102 or distal vertex 103.

Figures 9A, 9B, 9C:
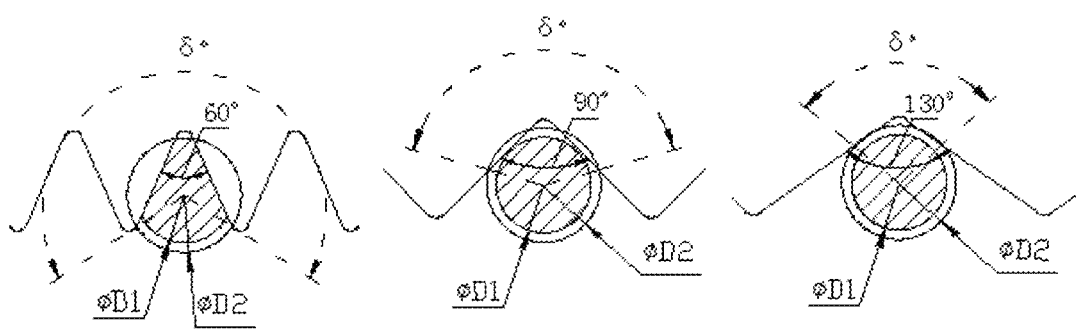
FIG. 9a is a schematic diagram of the stent graft shown in FIG. 1 with a wave included angle being 60°.
FIG. 9b is a schematic diagram of the stent graft shown in FIG. 1 with a wave included angle being 90°.
FIG. 9c is a schematic diagram of the stent graft shown in FIG. 1 with a wave included angle being 130°.

When in-situ fenestration is carried out on the stent graft, a puncture device is used to puncture a small hole in the stent graft, and the small hole is dilated to a required size by the use of a balloon. Referring to FIGS. 9a, 9b and 9c, the wave heights of the wavy rings 101 in FIGS. 9a, 9b and 9c are the same, and the wave included angles are 60°, 90° and 130°, respectively. A balloon with a diameter of D1 (preferably D1 being 3-18 mm) is used to expand a circle of the same size at the corresponding position of each wavy ring 101, where the corresponding position herein refers to a position where the distance of a connecting line, in the axis direction of the stent graft, between the circle center of the balloon and a proximal vertex of the wavy ring 101 in each of FIGS. 9a, 9b and 9c, is equal. The hatched lines in the figures indicate the shapes of windows expanded by the balloon, and it can be seen from the figures that when the wave included angle is 90° or 130°, the windows meeting the size requirements may be expanded, while the wavy ring 101 with the wave included angle being 60° may limit the fenestration size so that a fenestration edge follows the wavy ring 101. In the figures, the region of the wavy ring 101 covered by a circle with a diameter of D2 (D2=110% D1) is a region where the wavy ring 101 supports the fenestration edge, that is, the greater the corresponding angle δ of an intersection of the wavy ring 101 and the circle with the diameter of D2, the higher the supporting effect that the wavy ring 101 provides for the fenestration edge. As can be seen from the figures, the larger the wave included angle, the smaller the corresponding angle δ of the intersection of the wavy ring 101 and the circle with the diameter of D2, leading to a failure to provide sufficient support for the fenestration edge by the wavy ring 101.

As can be seen from the above, when the wave included angle of the wavy ring 101 in a certain region is large, the wavy ring 101 does not limit the fenestration size, thereby being beneficial to the fenestration; however, if the wave included angle is too large, the fenestration edge is caused to be far away from the wavy ring 101, and the wavy ring 101 cannot provide enough support for the fenestration edge; and if the fenestration edge lacks the support from the wavy ring 101, the window may be further expanded under the action of a radial force of a branch stent, finally leading to the separation of the branch stent from the stent graft. In addition, if the wave included angle of the wavy ring 101 is too large, the number of waves distributed in the circumferential direction of the stent graft in the region is too small, which is not conducive to maintaining the tubular cavity shape of the stent graft. However, when the wave included angle of the wavy ring 101 in a certain region is small, although enough support may be provided for the fenestration edge, the fenestration size may be limited, so that the fenestration size does not meet the size of a branch vessel. In addition, the wavy ring 101 has a certain rigidity and is not prone to deformation under the action of external force, and after a fenestration device is abutted against the wavy ring 101, the wavy ring 101 is easily broken, or the wavy ring 101 is excessively displaced with respect to the membrane 200, so that the radial supporting effect of the stent graft is affected.

According to the application, with the arrangement of the keel regions 100*a* and the non-keel region 100*b* with different shortening rates in the circumferential direction of the stent graft, and the adjustment on the wave included angles of the keel regions 100*a* and the non-keel region 100*b*, the non-keel region 100*b* can meet the requirements of in-situ fenestration, and the keel regions 100*a* can meet the requirement of axial supporting force, so that the stent graft is prevented from shortening into a tumor cavity.

A plurality of second wavy segments of the non-keel region 100*b* are arranged in a spaced manner in the axial direction, and when the adjacent second wavy segments are different in phase, the areas available for fenestration between the adjacent second wavy segments are different. FIGS. 10*a*, 10*b* and 10*c* are sequential schematic diagrams of the adjacent second wavy segments being opposite in phase, being identical in phase, and having a phase difference, in the case that the wave structures and wave spacings of the adjacent second wavy segments are identical when the adjacent first wavy segments have no overlap in the axial direction. The term "being opposite in phase" means that the wave crests of the second wavy segment are opposite to the wave troughs of the adjacent second wavy segment, the term "being identical in phase" means that the wave crests of the second wavy segment are opposite to the wave crests of the adjacent second wavy segment, and the "phase difference" means that the wave crests of the second wavy segment are staggered with the wave crests and troughs of the adjacent second wavy segment. As can be seen from the figures, when the adjacent second wavy segments are opposite in phase, the area available for fenestration between the adjacent second wavy segments is at a maximum, and when the adjacent second wavy segments are identical in phase, the area available for fenestration is at a minimum. However, when the adjacent second wavy segments are identical in phase, fenestration regions are distributed more uniformly.

In order to meet the fenestration requirement of the stent graft, different phase conditions may be adapted by adjusting the wave height and the ratio of the wave height to the wave spacing of the second wavy segment of the non-keel region 100*b*. In the case that the second wavy segments have no overlap in the axial direction, when the connecting line between the wave crest of the second wavy segment and the corresponding wave crest of the adjacent second wavy segment is parallel to a rail of the stent graft, the ratio of the wave height of the second wavy segment to the spacing between the adjacent second wavy segments is ⅓-1, and the wave height of the second wavy segment is 4-12 mm. When the connecting line between the wave crest of the second wavy segment and the corresponding wave trough of the adjacent second wavy segment is parallel to the rail of the stent graft, the ratio of the wave height of the second wavy segment to the spacing between the adjacent second wavy segments is ¼-¾, and the wave height of the second wavy segment is 4-14 mm. When the connecting line between the wave crest of the second wavy segment and the corresponding wave crest of the adjacent second wavy segment is inclined with respect to the rail of the stent graft, the ratio of the wave crest of the second wavy segment to the spacing between the adjacent second wavy segments is ¼-1, and the wave height of the second wavy segment is 4-14 mm. As shown in conjunction with FIG. 11, in the case that the adjacent second wavy segments have overlaps in the axial direction, the ratio of the wave height of the second wavy segment to the spacing between the adjacent second wavy segments is 1-3, and the wave height of the second wavy segment is 5-15 mm. The corresponding wave crest here refers to the wave crest of the adjacent second wavy segment that has the shortest connecting distance between the wave crest of the second wavy segment and a wave crest of the adjacent second wavy segment compared to other wave crests of the adjacent second wavy segment; and the corresponding wave trough here refers to the wave trough of the adjacent second wavy segment that has the shortest connecting distance between the wave trough of the second wavy segment and the wave trough of the adjacent second wavy segment compared to other wave troughs of the adjacent second wavy segment.

As shown in FIG. 8, the non-keel region 100*b* includes two sub-regions, namely a greater curvature side region 110 and a lesser curvature side region 111, that are distributed in the circumferential direction. The wave included angle of the greater curvature side region 110 is 80°-100°, preferably 90°, and the wave included angle of the lesser curvature side region 111 is 75°-95°, preferably 80°. The ratio of the wave height of the second wavy segment on the greater curvature side region 110 to the wave height of the second wavy segment on the lesser curvature side region 111 is 0.7-1, the ratio of the wave spacing between the adjacent second wavy segments on the greater curvature side region 110 to the wave spacing on the lesser curvature side region 111 is 0.7-1, and the ratio of the area covered by the greater curvature side region 110 on the outer surface of the stent graft to the area covered by the lesser curvature side region 111 on the outer surface of the stent graft is 0.7-1.3. In the illustrated embodiment, the ratio of the area covered by the greater curvature side region 110 on the outer surface of the stent graft is equal to the area covered by the lesser curvature side region 111 on the outer surface of the stent graft, the wave heights of the second wavy segments on the greater curvature side region 110 are equal, and the wave spacings between the adjacent second wavy segments on the greater curvature side region 110 are equal. Also, the wave heights of the second wavy segments on the lesser curvature side region 111 are equal, and the wave spacings between the adjacent second wavy segments on the lesser curvature side region 111 are equal.

In the illustrated embodiment, the greater curvature side region 110 and the lesser curvature side region 111 are disposed opposite to each other in the circumferential direction, and the keel regions 100*a* are connected between the greater curvature side region 110 and the lesser curvature side region 111. It will be appreciated that the non-keel region 100*b* may also be divided into three or more circumferentially distributed sub-regions as desired, the sub-regions may be arranged in a spaced manner or continuously, and the wave shapes, the number of waves, the wave heights, and the wave angles of the wavy segments of each sub-region may be set as desired.

Further, referring to FIGS. 1 and 2, the stent graft further includes at least one proximal wavy ring 101*a* at one end of the plurality of wavy rings 101.

The axial shortening rate between the proximal wavy ring 101*a* and its adjacent wavy ring 101 is less than 10%, so as to enhance the axial supporting effects of the end portions of the stent graft, and to prevent the two ends of the stent graft from causing the stent graft to swing under the impact of the blood flow.

When the number of the proximal wavy rings 101*a* is two or more, the axial shortening rate between the two or more proximal wavy rings 101*a* is less than 3%, so as to enhance the axial supporting effect of the end portions of the stent graft, and to prevent the end portions of the stent graft from causing the stent graft to swing under the impact of the blood flow. Preferably, the axial shortening rate between the two or more proximal wavy rings 101a is zero.

It will be appreciated that at least one distal wavy ring (not shown) may be disposed at the other end of the plurality of wavy rings 101 and the axial shortening rate between the distal wavy ring and the adjacent wavy ring 101 is less than 10%. When the number of the distal wavy rings is two or more, the axial shortening rate between the two or more distal wavy rings is less than 3%, preferably 0.

Both the proximal wavy ring and the distal wavy ring are made of materials having good biocompatibility, such as nickel titanium, stainless steel or the like. The proximal wavy ring and the distal wavy ring both have closed cylindrical structures. The proximal wavy ring and the distal wavy ring may be a Z-shaped wave, an M-shaped wave, a V-shaped wave or sinusoidal wave structures, or of other structures that are radially compressible to a very small diameter. It will be appreciated that not only the numbers of the proximal wavy ring and the distal wavy ring may be set as desired, but also the wave shapes, the number of waves, and the wave heights of the proximal wavy ring and the distal wavy ring may be set as desired.

Further, the stent graft further includes an anchoring bare stent 105 located at one end or the distal end of the stent graft and connected with the proximal wavy ring or the distal wavy ring.

FIG. 12 shows a stent graft provided by a second preferred embodiment of the present disclosure, which differs from the first embodiment in that each keel region 100a includes one first proximal vertex 102a, and the connecting line between the first proximal vertices 102a of two adjacent wavy rings 101 is inclined with respect to the axis of the stent graft.

FIG. 13 shows a stent graft provided by a third preferred embodiment of the present disclosure, which differs from the first embodiment in that the wavy ring 101 further includes a third wavy segment in the keel region 100a. The wave height L1 of the first wavy segment is greater than the wave height L6 of the third wavy segment.

The third wavy segment includes at least one third proximal vertex 102c, at least one third distal vertex 103c, and a third supporting body 104c connecting the adjacent third proximal vertex 102c and third distal vertex 103c, and the wave height L6 of the third wavy segment refers to the axial distance between third proximal vertex 102c and the third distal vertex 103c.

In the illustrated embodiment, the wave height L6 of the third wavy segment is equal to the wave height L2 of the second wavy segment, and the first distal vertex 103a, the second distal vertex 103b, and the third distal vertex 103c are located in the same plane perpendicular to the longitudinal central axis of the stent graft. It will be appreciated that, in other embodiments, the wave height L6 of the third wavy segment and the wave height L2 of the second wavy segment may also be unequal, and the first distal vertex 103a, the second distal vertex 103b and the third distal vertex 103c need not be located in the same plane perpendicular to the longitudinal central axis of the stent graft.

Figure 14:
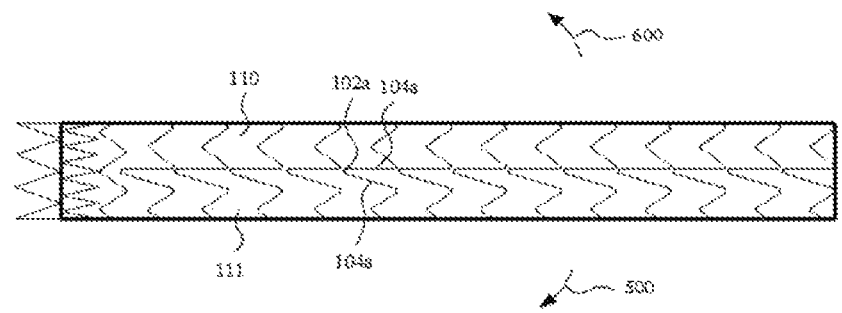
FIG. 14 is a structural schematic diagram of a stent graft provided by a fourth preferred embodiment of the present disclosure.

FIG. 14 shows a stent graft provided by a fourth preferred embodiment of the present disclosure, which differs from the first embodiment in that the first supporting bodies 104a that are connected to one side of the first proximal vertices 102a and close to the greater curvature side region 110 are distributed in the axial direction parallel to the stent graft, and the first supporting bodies 104a that are connected to the other side of the first proximal vertices 102a and close to the lesser curvature side region 111 are disposed obliquely with respect to the axis direction of the stent graft.

Figure 15:
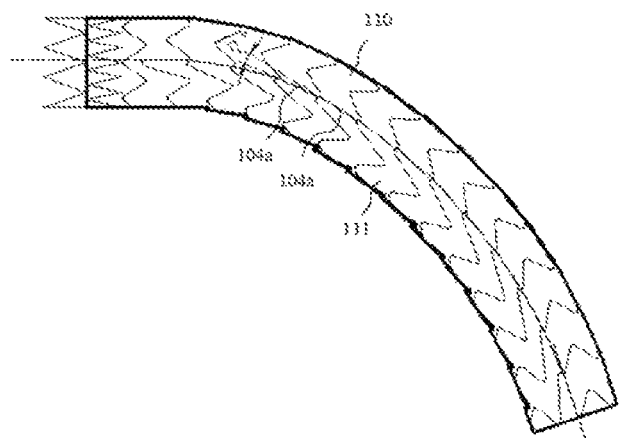
FIG. 15 is a structural schematic diagram of the stent graft shown in FIG. 14 after being bent in a direction indicated by a first arrow.
Figure 16:
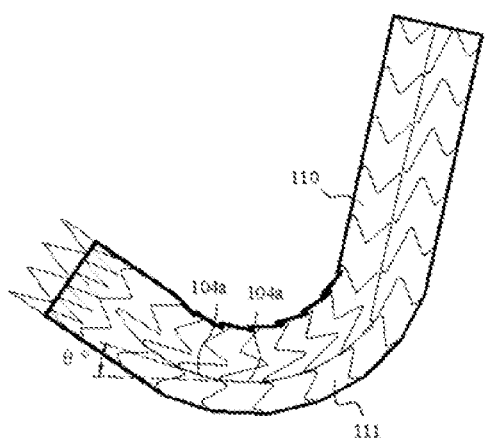
FIG. 16 is a structural schematic diagram of the stent graft shown in FIG. 14 after being bent in a direction indicated by a second arrow.

When the stent graft of FIG. 14 is bent in a direction indicated by a first arrow 500, referring to FIG. 15, the first supporting bodies 104a adjacent to the greater curvature side region 110 of the adjacent first wavy segments abut against each other to form an axial support, and the included angle between the first supporting bodies 104a adjacent to the greater curvature side region 110 of the adjacent first wavy segments is η°. When the stent graft of FIG. 14 is bent in a direction indicated by a second arrow 600, referring to FIG. 16, the first supporting bodies 104a adjacent to the lesser curvature side region 111 of the adjacent first wavy segments abut against each other to form an axial support, and the included angle between the first supporting bodies 104a adjacent to the lesser curvature side region 111 of the adjacent first wavy segments is θ°. As can be seen from the figures, η° is less than θ°. When the first supporting bodies 104a of the adjacent first wavy segments abut against each other to form the axial support, the greater the included angle between the first supporting bodies 104a of the adjacent first wavy segments, the smaller the force distributed to the axial direction of the stent graft, and the poorer the axial supporting effect on the stent graft. Therefore, the axial supporting effect formed when the first supporting bodies 104a are distributed parallel to the axial direction of the stent graft abutting against each other in FIG. 15 is superior to the axial supporting effect formed when the first supporting bodies 104a are disposed obliquely with respect to the axial direction of the stent graft abutting against each other in FIG. 16. Meanwhile, when the included angle between the first supporting bodies 104a of the adjacent first wavy segments is greater, excessive deformation of the membranes of the keel regions 100a is easily caused to bring about an uneven surface of the stent graft, thus leading to a high probability of thrombosis.

When the first supporting bodies 104a distributed in the axial direction parallel to the stent graft abut against each other to form the axial support, the included angle between the first supporting bodies 104a of the adjacent first wavy segments is the smallest, and the axial supporting force of the stent graft is the highest. Therefore, the first supporting bodies 104a distributed in the axial direction parallel to the stent graft are disposed on one side close to the greater curvature side region 110, and when the stent graft is bent towards the lesser curvature side, the first supporting bodies may provide enough axial supporting force for the stent graft, and the axial supporting effect on the stent graft is optimal.

Figure 17:
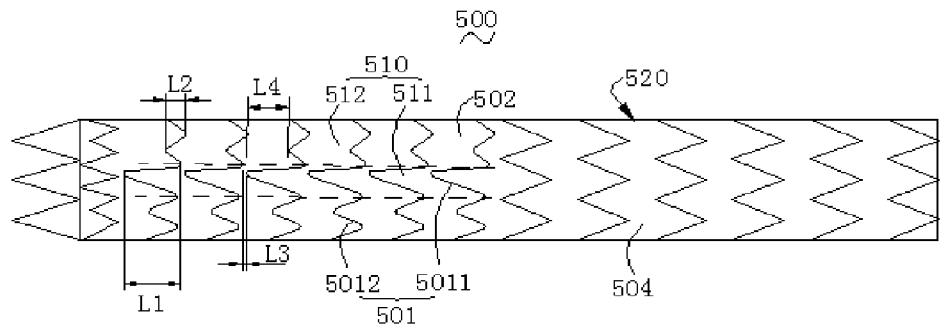
FIG. 17 is a structural schematic diagram of a stent graft according to a fifth embodiment of the present disclosure.

Referring to FIG. 17, a fifth preferred embodiment of the present disclosure provides a stent graft 500, including a first body section 510 and a second body section 520 connected with the first body section 510, which are distributed in the axial direction. The axial shortening rate of the first body section 510 is 10-40%, and the axial shortening rate of the second body section 520 is zero. The axial shortening rate of the first body section 510 is measured by a method including the following steps of: in a natural state, taking the length of the first body section 510 as a and the diameter as d, surrounding the first body section 510 with an inner tube with a diameter of 0.9d, applying pressure of 1-2N in the axial direction to two ends of the first body section 510 until no shortening (no folding) occurs to obtain the length b, and calculating the axial shortening rate of the first body section 510 according to the formula (a−b)*100%/a. When the length of the first body section 510 reaches (a−b), a rigid axial support may be formed on the first body section 510.

In use, the first body section 510 is placed into a bent section (a position where the curvature radius is smaller) of the aortic arch, and the second body section 520 is placed into a straight section (a position where the curvature radius is greater) of the aortic arch. The first body section 510 can axially shorten, that is, the first body section 510 has certain flexibility in the axial direction, so that the first body section 510 generates no straightening force while conforming to the bent configuration of the aortic arch, so that the safety of the operation is improved. However, the second body section 520 cannot axially shorten, so that the second body section 520 can be prevented from shortening under the action of the blood flow, and the end portions of the second body section 520 are prevented from retracting into the tumor cavity to endanger the life of a patient. Preferably, the axial shortening rate of the first body section 510 is 20-30%, so that the first body section 510 can better conform to the bent configuration of the aortic arch, and a relatively stable axial supporting structure can be formed, thereby reducing the risk of shortening of the first body section 610 after implantation.

In the present embodiment, the length of the first body section 510 is 50-100 mm, so that the first body section 510 is able to cover the bent section in the aortic arch.

Figure 18:
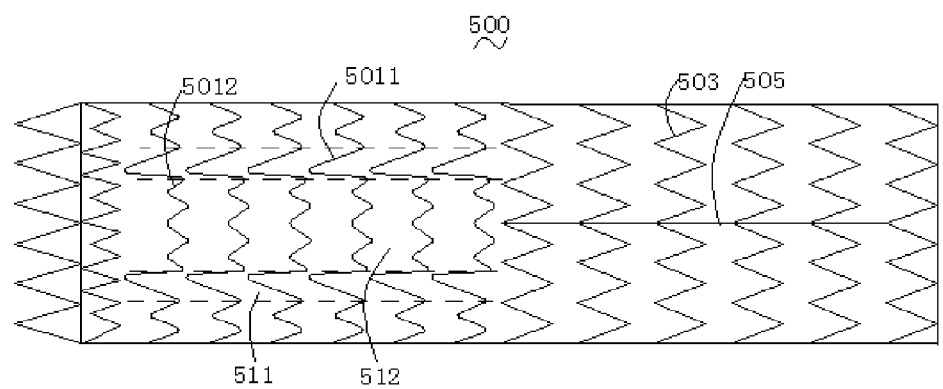
FIG. 18 is a structural schematic diagram of the stent graft shown in FIG. 17 after being expanded.

Specifically, the first body section 510 and the second body section 520 are both open-ended and hollow straight tubular structures. Referring together to FIG. 18, the first body section 510 includes a plurality of first wave loops 501 arranged in a spaced manner in the axial direction and a first membrane 502 covering the first wave loops 501. The second body section 520 includes a plurality of second wave loops 503 arranged in the axial direction, a connector 505 connecting the adjacent second wave loops 503, and a second membrane 504 covering the second wave loops 503 and the connector 505. The first membrane 502 and the second membrane 504 are tubular cavity structures that are closed in the center and are open-ended, and are made of high molecular materials having good biocompatibility, such as e-PTFE, PET, or the like. The first membrane 502 which is fixed to the first wave loops 501, and the second membrane 504 which is fixed to the second wave loops 503 and the connector 505, are respectively enclosed to form a tube cavity with a longitudinal axis, and after the stent graft is implanted into a blood vessel, the tube cavity serves as a channel through which blood flows. The first wave loops 501, the second wave loops 503 and the connector 505 are made of materials having good biocompatibility, such as nickel titanium, 316L medical stainless steel, or the like. The first wave loops 501 and the second wave loops 503 may be a Z-shaped wave, an M-shaped wave, a V-shaped wave or sinusoidal wave structures, or of other structures that are radially compressible to a very small diameter. In actual preparation, the closed first wave loops 501 and second wave loops 503 are formed by weaving nickel-titanium wires or cutting and shaping nickel-titanium tubes, with surfaces of the first wave loops 501 and the second wave loops 503 covered with membranes, and the first wave loops 501 and the second wave loops 503 are respectively fixed to the first membrane 502 and the second membrane. 504 by means of sewing or high-temperature pressurization, or the like.

It should be noted that the first body section 510 and the second body section 520 are only distinguished for convenience of explanation and do not mean that the connection boundary of the stent graft 500 is broken, and the first body section 510 and the second body section 520 are of an integral structure, that is, the first membrane 502 and the second membrane 504 may be of an integral structure.

With continued reference to FIG. 17, the first body section 510 includes, in a circumferential direction, keel regions 511 and a non-keel region 512 connected with the keel regions 511, where the axial shortening rates of the keel regions 511 are less than the axial shortening rate of the non-keel region 512, and the axial shortening rates of the keel regions 511 are 10-40%. When the first body section 510 is bent, a rigid axial supporting structure may be formed in the keel regions 511. Referring together to FIG. 18, the number of the keel regions 511 is two, and the two keel regions 511 are substantially symmetrically distributed along the connector 505, so that the first body section 510 may better conform to the anatomical structure of the aortic arch. The first body section 510 is prevented from generating additional stress and twisting forces during bending, the first body section 510 is prevented from swinging under the action of the blood flow, the stability of the first body section 510 is improved in the bent state, and the life of the stent graft 500 may be prolonged. It should be noted that the statement that the two keel regions 511 are substantially symmetrically distributed along the connector 505 means that the difference between the distances from center lines of the two keel regions 511 to the connector 505 may have a deviation of 5%.

Specifically, the first wave loops 501 include first wavy segments 5011 located in the keel regions 511 and second wavy segments 5012 located in the non-keel region 512, the wave height L1 of the first wavy segment 5011 is greater than the wave height L2 of the second wavy segment 5012, the wave spacing L3 between two adjacent first wavy segments 5011 is less than the wave spacing L4 between two adjacent second wavy segments 5012, and the first wavy segments 5011 of the two keel regions 511 are substantially symmetrically distributed along the connector 505. The first wavy segment 5011 and the second wavy segment 5012 each include wave crests, wave troughs, and wave rods connecting the adjacent wave crests and troughs. When the first body section 510 is bent, the wave crests and the wave troughs of the first wavy sections 5011 abut against each other to form an axial support, and a relatively large region for fenestration is provided between the second wavy sections 5012, so that the implantation of a branch stent in the region of the second wavy sections 5012 is facilitated. It should be noted that the wave height of the present application refers to the distance in the axial direction between a wave crest and an adjacent wave trough, and the wave spacing refers to the axial distance between a wave crest and a corresponding wave trough (a wave trough closest to the wave crest) of an adjacent wave loop. Preferably, the ratio of the wave height of the first wavy segment 5011 to the wave height of the second wavy segment 5012 is not greater than 3, and the connecting line between the wave trough of the first wavy segment 5011 of the first wave loop 501 and the wave trough of the second wavy segment 5012 is perpendicular to the plane of the axis of the first body section 510.

In the illustrated embodiment, the wave heights of the plurality of first wavy segments 5011 are equal, and the wave spacings between every two adjacent first wavy segments 5011 are equal. The wave heights of the plurality of second wavy segments 5012 are also equal, and the wave spacings between every two adjacent second wavy segments 5012 are also equal. The connecting line of the corresponding wave crests of the plurality of first wavy segments 5011 is parallel to the axis of the first body section 510. Specifically, the wave height L1 of the first wavy segment 5011 is 6-16 mm, and the wave height L2 of the second wavy segment 5012 is 4-12 mm.

Further, in order to facilitate fenestration in the non-keel region 512, the included angle between two adjacent wave rods of the second wavy segment 5012 is 80°-100°, so that the area available for fenestration between the two adjacent wave rods is large, and the limitation of the wave rods to the fenestration size is reduced. Preferably, the included angle between two adjacent wave rods of the second wavy segment 5012 is 90°.

Further, the phase difference of the second wavy segment 5012 is zero, that is, the connecting line between the two corresponding wave crests of the adjacent second wavy segment 5012 is parallel to the axis of the first body section 510, and the connecting line between the two corresponding wave troughs of the adjacent second wavy segment 5012 is parallel to the axis of the first body section 510. In this way, the shortest distance between any two points on the two adjacent second wavy segments 5012 is large, so that portions available for fenestration in the non-keel region 512 of the first body section 510 are uniformly distributed, the fenestration of the first body section 510 in all positions in the non-keel region 512 is facilitated, and the implantation of the branch stent into the first body section 510 is also facilitated.

With continued reference to FIG. 18, the included angle between the wave rod of the first wavy segment 5011 close to the connector 505 and the axial direction of the first body section 510 is less than the included angle between the wave rod away from the connector 505 and the axial direction of the first body section 510. After the stent graft 500 is released to the aortic arch, the included angle between the wave rods of the adjacent first wavy segments 5011 close to the connector 505 can be relatively small, so that the force distributed to the axial direction of the first body section 510 is relatively large, and the axial supporting effect of the first body section 510 is improved advantageously. Specifically, the included angle between the wave rod of the first wavy segment 5011 close to the connector 505 and the axial direction of the first body section 510 is not greater than 15°, and the included angle between the wave rod of the first wavy segment 5011 away from the connector 505 and the axial direction of the first body section 510 is between 20°-60°. Specifically, in the embodiment, the number of the wave rods of the first wavy segment 5011 is two, the included angle between the wave rod close to the connector 505 and the axial direction of the first body section 510 is zero, and the included angle between two adjacent wave rods is 30-60°.

Further, each keel region 511 covers an angle of 15°-45° in the circumferential direction, so that damage to the membranes during bending due to excessively sharp wave crests of the first wavy segments 5011 of the first body section 510 may be avoided, and the risk that the first body section 510 is folded during bending may also be reduced. Preferably, each keel region 511 covers an angle of 20°-30° in the circumferential direction.

Further, the included angle between the connecting line between a middle point of the wave rod of the first wavy segment 5011 close to the connector 505 and the longitudinal central axis of the first body section 510 and the connecting line between the connector 505 and the longitudinal central axis of the first body section 510 is 60°-90°, that is, the angle covered in the circumferential direction by the non-keel region 512 which is between the two keel regions 511 and on the side intersecting with the extension line of the connector 505 is approximately 120°-180°. After the implantation of the aortic arch, the area of the non-keel region 512 that is between the two keel regions 511 on the first body section 510 and located on the greater curvature side of the blood vessel can be relatively large, so that the fenestration on the non-keel region 512 on this side for the implantation of the branch stent is facilitated, and at the same time, the first body section 510 can better conform to the anatomical structure of the aortic arch.

It should be noted that the structure of the second body section 520 may be as shown in the prior art and will not be described in detail herein. In the illustrated embodiment, the shapes and sizes of the second wave loops 503 are identical, and the spacings between two adjacent second wave loops 503 are also equal. The wave heights of the second wave loops 503 are 8-18 mm, and the ratio of the wave spacing to the wave height of two adjacent second wave loops 503 is not greater than ⅓. The number of the connector 505 is one, the connector 505 is linear, and the connector 505 spans all of the second wave loops 503 of the second body section 520.

It will be appreciated that the second wave loops 503 of the second body section 520 and the connector 505 may also be adjusted according to actual needs, as long as it is ensured that the shortening rate of the second body section 520 is zero.

Figure 19:
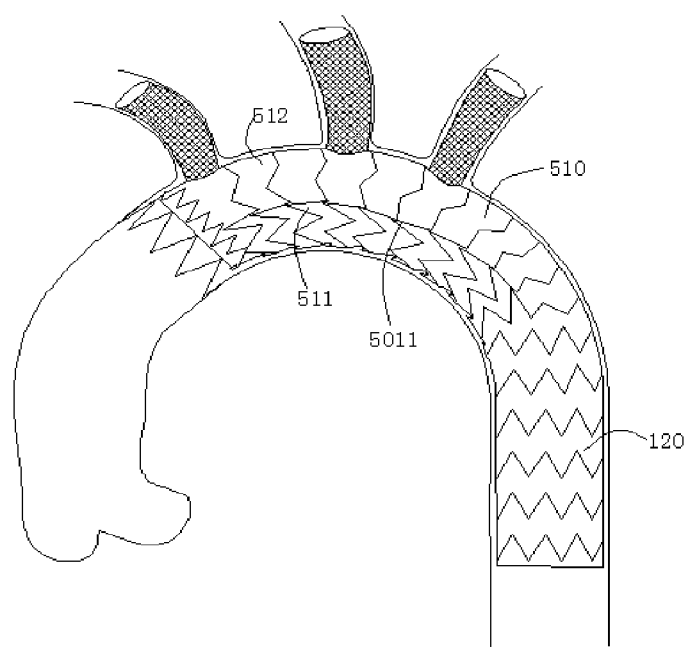
FIG. 19 is a structural schematic diagram of the stent graft shown in FIG. 17 after being implanted into an aortic arch.

Referring together to FIG. 19, in an actual operation, when the stent graft 500 is implanted into the aortic arch, the first body section 510 may be located at a bent portion of the aortic arch, the second body section 520 may be located at a straight portion of the aortic arch, the first wavy segments 5011 of the keel regions 511 may abut against each other to form an axial support, and reconstruction of important branch vessels of three main arteries, including the truncus brachiocephalicus, the left common carotid artery and the left subclavian artery, on the aortic arch may be accomplished by means of in-situ fenestration on the non-keel region 512 located on the greater curvature side of the blood vessel.

Figure 20:
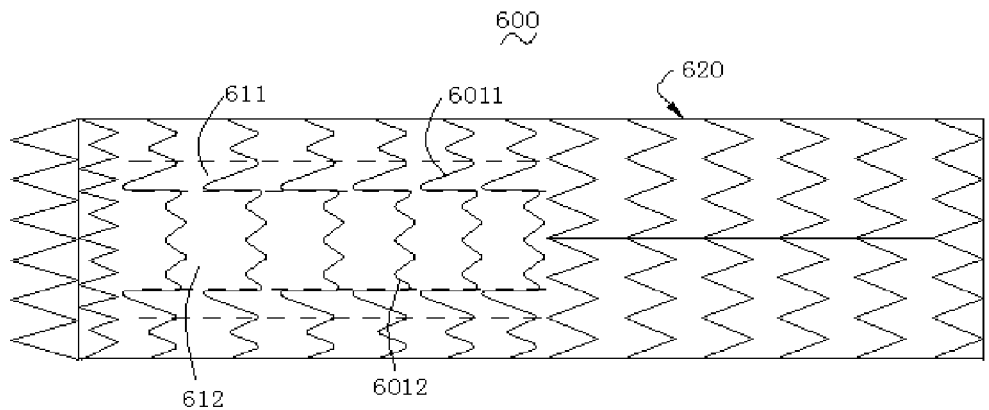
FIG. 20 is a structural schematic diagram of a stent graft according to a sixth embodiment of the present disclosure.

Referring to FIG. 20, the structure of the stent graft 600 according to the second embodiment of the present disclosure is substantially the same as that of the stent graft 500, except that first wave loops 601 of a first body section 610 are arranged at unequal intervals.

Figure 21:
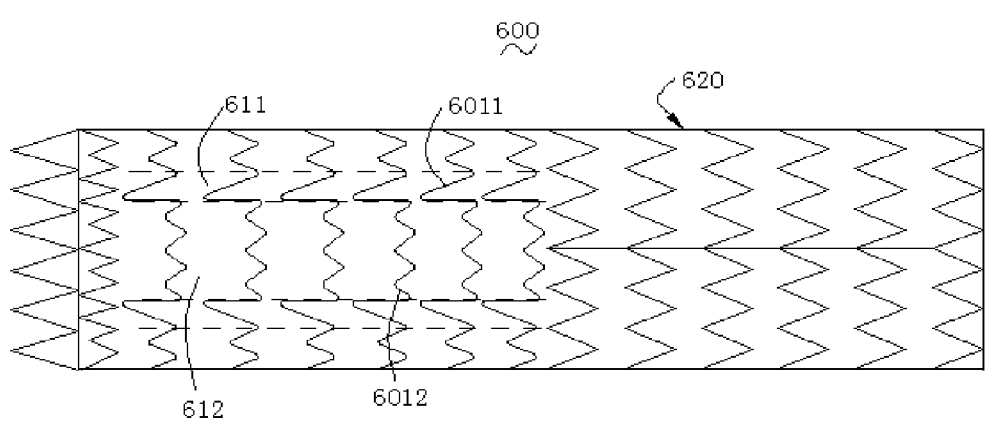
FIG. 21 is a structural schematic diagram of the stent graft shown in FIG. 20 after being expanded.

Referring together to FIG. 21, the wave spacing between first wavy segments 6011 of a keel region 611 is gradually reduced from an end away from the second body section 620 to an end close to the second body section 620, so that the axial shortening rate of the first body section 610 is gradually reduced from the end away from the second body section 620 to the end close to the second body section 620, gentle transition to the second body section 620 is achieved, the risk of local compression of a vessel wall caused by the fact that a region where the first body section 610 is connected with the second body section 620 is bulged can be reduced, and the stability of the stent graft 600 is improved. Further, the wave spacing between second wavy segments 6012 of a non-keel region 612 is gradually reduced from an end away from the second body section 620 to an end close to the second body section 620, so that a window more meeting the size requirement of a branch vessel on the aortic arch can be conveniently opened in the non-keel region 612, and the improvement of the stability of the branch stent and the stent graft 600 is facilitated.

In the illustrated embodiment, the wave spacing between the first wavy segments 6011 of the keel region 611 is an arithmetic sequence from the end away from the second body section 620 to the end close the second body section 620. The wave spacing between the second wavy segments 6012 of the non-keel region 612 is an arithmetic sequence from the end away from the second body section 620 to the end close to the second body section 620. Specifically, from the end close to the second body section 620, the wave spacing between the first wavy segment 6011 and the second first wavy segment 6011 is 1 mm, the wave spacing between the second first wavy segment 6011 and the third first wavy segment 6011 is 2 mm, and so on.

It will be appreciated that, in other embodiments, the wave spacing between the first wavy segments 6011 of the keel region 611 may also be adjusted as desired, so long as the shortening rate of the keel region 611 is between 10% and 40%. The wave spacing between the second wavy segments 6012 of the non-keel region 212 may also be adjusted according to the position and size of the branch vessel on the aortic arch.

Figure 22:
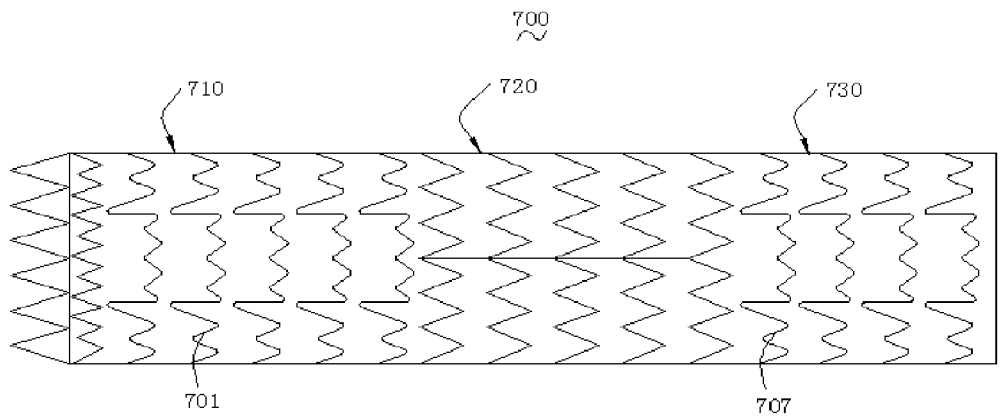
FIG. 22 is a structural schematic diagram of a stent graft according to a seventh embodiment of the present disclosure.

Referring to FIG. 22, the structure of a stent graft 700 according to a third embodiment of the present disclosure is substantially the same as that of the stent graft 500, except that the stent graft 700 further includes a third body section 730 connected to an end of the second body section 720 away from the first body section 710. The axial shortening rate of the third body section 730 is less than the shortening rate of the first body section 710, and greater than the axial shortening rate of the second body section 720.

Although the straight section of the aortic arch is in a relatively gentle (relatively large curvature radius) region in the blood vessel, due to the relatively complicated anatomical structure of the aortic arch, a part of residual straightening force may still exist after the implantation of the second body section 720; and with the arrangement of the third body section 730 which has an anchoring effect with a vessel wall, a certain stretch restriction effect may be played on the second body section 720 to reduce the acting force of the second body section 720 on the vessel wall, so that the risk of a rupture of the vessel wall is reduced. In addition, the axial shortening rate of the third body section 730 is less than the axial shortening rate of the first body section 710 and greater than the axial shortening rate of the second body section 720, so that the third body section 730 has a certain bending characteristic and can be prevented from shortening.

With continued reference to FIG. 22, the third body section 730 includes a plurality of third wave loops 707 arranged in a spaced manner in the axial direction, and the wave spacing between the third wave loops 707 is gradually increased from the end close to the second body section 720 to the end away from the second body section 720, so that a gentle transition between the second body section 720 and the third body section 730 is achieved, thereby reducing the risk that the stent graft 700 is bulged in use.

The structure of the third body section 730 may be similar to the structure of the first body section 710, and is not described in detail herein. In the illustrated embodiment, the structure of the third wave loop 707 may be the same as that of the first wave loop 701, and the third body section 730 with a smaller axial shortening rate may be obtained by reducing the wave spacing of the first wave loop 701. It will be appreciated that, in other embodiments, the structure of the third body section 730 may also be designed as desired, so long as the axial shortening rate of the third body section 730 is maintained between the axial shortening rate of the first body section 710 and the axial shortening rate of the second body section 720. For example, the connecting line of the wave crests of each third wave loop 707 is located in a plane perpendicular to the axis of the third body section 730, and the connecting line of the wave troughs is also located in the plane perpendicular to the axis of the third body section 730.

The technical features of the above-mentioned embodiments may be combined in any combination. In the interest of brevity, all possible combinations of the technical features in the above embodiments are not described, but all should be considered as within the scope of this Description, except combinations where at least some of such technical features are mutually exclusive.

The above-mentioned embodiments are merely illustrative of several embodiments of the present disclosure, and the description thereof is more specific and detailed, but is not to be construed as limiting the scope of protection of the present disclosure. It should be noted that several modifications and improvements can be made by those ordinarily skilled in the art without departing from the concept of the present disclosure, which fall within the scope of protection of the present disclosure. Therefore, the scope of protection of the present disclosure shall be subject to the appended claims.

The invention claimed is:

1. A stent graft, comprising a plurality of wavy rings and membranes connected and fixed to the plurality of wavy rings, wherein the stent graft comprises, in a circumferential direction, a plurality of longitudinal keel regions and a non-keel region connected with a keel region, and in a longitudinal direction, each of the plurality of keel regions is directly connected to another keel region, wherein the axial shortening rate of the keel regions is less than the axial shortening rate of the non-keel region;

wherein the non-keel region has a greater curvature side region distributed in the circumferential direction, and a lesser curvature side region distributed in the circumferential direction, and wherein the greater curvature side region and the lesser curvature side region are disposed opposite to each other in the circumferential direction, and the plurality of keel regions is connected between the greater curvature side region and the lesser curvature side region.

2. The stent graft of claim 1, wherein each keel region covers a circumferential angle of from 15° to 45° on the stent graft.

3. The stent graft of claim 2, wherein the number of the plurality of keel regions is two, and the two keel regions are symmetrically disposed in the circumferential direction of the stent graft.

4. The stent graft of claim 1, wherein the wavy rings comprise first wavy segments located in the plurality of keel regions and second wavy segments located in the non-keel region, and the wave heights of the first wavy segments are greater than the wave heights of the second wavy segments.

5. The stent graft of claim 4, wherein the wave height of the first wavy segment is L1, the wave height of the second wavy segment is L2, and L2/L1 is greater than or equal to ⅓ and less than 1.

6. The stent graft of claim 5, wherein L2 is greater than or equal to 4 mm and less than or equal to 12 mm, and L1 is greater than or equal to 8 mm and less than or equal to 18 mm.

7. The stent graft of claim 5, wherein the spacing between the adjacent first wavy segments is L3, and L3/L1 is greater than or equal to ¼ and less than or equal to 3/2.

8. The stent graft of claim 7, wherein the first wavy segments comprise first proximal vertices, and a connecting line between the first proximal vertices of two adjacent first wavy segments is parallel to the axis of the stent graft.

9. The stent graft of claim 8, wherein the first wavy segment further comprises first supporting bodies connected with two sides of the first proximal vertices, the first supporting bodies located on one side of the first proximal vertices are distributed in the axial direction parallel to the stent graft, and the first supporting bodies located on the other side of the first proximal vertices are disposed obliquely with respect to the axial direction of the stent graft.

10. A stent graft, comprising a plurality of wavy rings and membranes connected and fixed to the plurality of wavy rings, wherein the stent graft comprises, in a circumferential direction, a plurality of longitudinal keel regions and a non-keel region connected with a keel region, and in a longitudinal direction, each of the plurality of keel regions is directly connected to another keel region, wherein the axial shortening rate of the keel regions is less than the axial shortening rate of the non-keel region, and the axial shortening rate of the keel region is from 10% to 40%;
 wherein the non-keel region has a greater curvature side region distributed in the circumferential direction, and a lesser curvature side region distributed in the circumferential direction, and wherein the greater curvature side region and the lesser curvature side region are disposed opposite to each other in the circumferential direction, and the plurality of one keel regions is connected between the greater curvature side region and the lesser curvature side region.

\* \* \* \* \*